US009669061B2

(12) United States Patent
Roschin et al.

(10) Patent No.: US 9,669,061 B2
(45) Date of Patent: Jun. 6, 2017

(54) **MEDICINAL AGENT EXHIBITING ANTIPROTOZOAL ACTIVITY TO *TRICHOMONAS VAGINALIS* IN AN IN-VITRO MODEL SYSTEM**

(75) Inventors: Viktor Ivanovich Roschin, St. Petersburg (RU); Vagif Sultanovich Sultanov, St. Petersburg (RU); Anatolii Borisovich Zhebrun, St. Petersburg (RU); Tamara Valentinovna Nikitina, St. Petersburg (RU); Lidija Borisovna Kuliashova, St. Petersburg (RU); Lludmila Aleksandrovna Berezina, St. Petersburg (RU)

(73) Assignees: Viktor Ivanovich Roschin, St. Petersburg (RU); Vagif Sultanovich Sultanov, St. Petersburg (RU)

( * ) Notice: Subject to any disclaimer, the term of this patent is extended or adjusted under 35 U.S.C. 154(b) by 0 days.

(21) Appl. No.: 12/992,751

(22) PCT Filed: May 5, 2009

(86) PCT No.: PCT/RU2009/000215
§ 371 (c)(1),
(2), (4) Date: Feb. 17, 2011

(87) PCT Pub. No.: WO2009/139665
PCT Pub. Date: Nov. 19, 2009

(65) Prior Publication Data
US 2011/0189321 A1    Aug. 4, 2011

(30) Foreign Application Priority Data
May 14, 2008    (RU) ................. 2008119139

(51) Int. Cl.
*A61K 36/13*    (2006.01)
*A61K 36/14*    (2006.01)
*A61K 36/15*    (2006.01)
*A61K 31/05*    (2006.01)

(52) U.S. Cl.
CPC .............. *A61K 36/15* (2013.01); *A61K 31/05* (2013.01)

(58) Field of Classification Search
CPC ......... A61K 36/13; A61K 36/14; A61K 36/15
USPC ........................................................ 424/770
See application file for complete search history.

(56) References Cited

U.S. PATENT DOCUMENTS

| 5,466,453 | A  | * | 11/1995 | Uchida et al. | ................. 424/735 |
| 2004/0235770 | A1 | * | 11/2004 | Davis et al. | ..................... 514/44 |
| 2006/0051384 | A1 | * | 3/2006 | Scholz et al. | ................. 424/405 |
| 2008/0253976 | A1 | * | 10/2008 | Scott et al. | ..................... 424/49 |
| 2009/0226541 | A1 | * | 9/2009 | Scholz et al. | ................. 424/672 |
| 2011/0039816 | A1 |   | 2/2011 | Roschin et al. | |

FOREIGN PATENT DOCUMENTS

| CN | 1102100 | * | 5/1995 |
| RO | 117895 | * | 9/2002 |
| RU | 2021803 | C1 | 10/1994 |
| RU | 2040266 | * | 7/1995 |
| RU | 2041646 | * | 8/1995 |
| RU | 2 208 950 | C2 | 7/2003 |
| RU | 2 272 626 | C1 | 3/2006 |
| SU | 1375226 | * | 2/1988 |

OTHER PUBLICATIONS

Alekseeva et al. Tr. Leningrad. Lesotekh. Akad. imeni S. M. Kirova. 1967. No. 100, p. 386, CAPLUS Abstract enclosed.*
Vil'ner et al. Sbornik Nauchnykh Rabot—Leningradskii Veterinaryi Institut. 1967. No. 28, pp. 751-757, CAPLUS Abstract enclosed.*
Zhou et al. Linchan Hyaxue Yu Gongye. 1993. vol. 13, No. 2, pp. 159-164, CAPLUS Abstract enclosed.*
King et al. Proc. Austral. Pig Sci. Assoc. 1999. vol. 242, one page, VETU Abstract enclosed.*
Document entitled "Solgaram Limited—Bioeffective™; Heralding a New Pharmaceutical Paradigm", Sep. 2007, 35 pages.*
Document entitled "Solgaram Limited—Company Announcement Bioeffective A Receives Formal TGA Approval", Feb. 2006, one page.*
Zhou et al. Linchan XHuaxue Yu Gongye. 1995. vol. 15, No. 1, pp. 51-56, CAPLUS Abstract enclosed.*
Petrin et al. Clin. Microbiol. Rev. 1998. vol. 11, No. 2, pp. 300-317.*
"Chlorophyll-carotene paste (coniferous)", 2004, http://www.sumtech.ru/bank/medicine/archive/pasta.htm.
Bespalov et al., "Coniferous Chlorophyll Carotene Paste A Review of Medical Applications," N. N,., Petrov State Scientific Research Institute of Oncology Federal Agency for Healthcare and Social Development of the Russian Federation, St. Petersburg, 2006, retrieved from the Internet: http://pineneedleresearch.com/media/CGNC_Dr_Bespalov_Review.pdf, retrieved Mar. 21, 2012.
Supplementary European Search Report issued Sep. 25, 2012 in application No. EP 09 74 6834 (corresponding to US 2011/0189321).
Office Action issued on Oct. 11, 2012 in U.S. Appl. No. 12/811,039.

(Continued)

*Primary Examiner* — Chris R Tate
(74) *Attorney, Agent, or Firm* — Foley & Lardner LLP

(57) ABSTRACT

The invention belongs in the field of medicine and can be used in the treatment of chronic and asymptomatic trichomonas infections of the urogenital tract.
The invention is consisted in development of new therapeutic substance of plant origin with minimal side effects for treatment of various forms of trichomonad infection.
The new therapeutic substance, of plant origin, is an olive coloured paste. It is composed of a conifer green needle complex (CGNC) and has a coniferous smell and antiprotozoal activity against *Trichomonas vaginalis* (when tested in an in vitro model).
At a concentration of 100 mg/ml CGNC has trichomonadocitic and trichomonadostatic properties. At 300 mg/ml it suppresses the growth of *T. vaginalis* and at 500 mg/ml it kills this organism.

8 Claims, No Drawings

(56) References Cited

OTHER PUBLICATIONS

Office Action issued on Apr. 26, 2013 in U.S. Appl. No. 12/811,039.
Office Action issued on Dec. 23, 2013 in U.S. Appl. No. 12/811,039.
Office Action issued on Jul. 17, 2014 in U.S. Appl. No. 12/811,039.
Bespalov et al., "Conifer Green Needle Complex in Patients with Precancerous Gastric Lesions: An Observational Pilot Study," Evidence-Based Complementary and Alternative Medicine, vol. 2016, Article ID 3848409, 12 pages, 2016.

* cited by examiner

MEDICINAL AGENT EXHIBITING ANTIPROTOZOAL ACTIVITY TO *TRICHOMONAS VAGINALIS* IN AN IN-VITRO MODEL SYSTEM

CROSS REFERENCE TO RELATED APPLICATIONS

This application is a National Stage of International Application No. PCT/RU2009/000215 filed on May 5, 2009, which claims priority from Russian Patent Application No. 2008-119139, filed on May 14, 2008, the contents of all of which are incorporated herein by reference in their entirety.

TECHNOLOGICAL FIELD

The invention belongs in the field of medicine and can be used in the treatment of chronic and asymptomatic trichomonas infections of the urogenital tract.

BACKGROUND OF INVENTION

*Trichomoniasis* is one of the most common sexually transmitted diseases of the urogenital tract. This infection has important medical and socio-economic significance because of the large numbers of people infected, often with a chronic form of the disease and relapses, and the caused damage to different organs and systems. World Health Organisation (WHO) data reveals that at the turn of the 20th and 21st centuries, almost half of all incidences of sexually transmitted infections were of trichomoniasis (Grodstein F. Relation of tubal infertility to a history of sexually transmitted diseases/F. Grodstein, M. B. Goldman, D. W. Cramer//Am. J. Epidemiol. —1993.—Vol. 137.—P. 577-584; Vilkki M., Pukkala E., Nieminen P. et al. Gynaecological infections as risk determinants of subsequent cervical neoplasia//Acta Oncol.-2000.—vol.—P. 71-75; Tikhomirov A. L. Urogenital trichomoniasis,/Tikhomirov A. L., Oleinik Ch. G.//Works of MGMSU-M., 2003, pp. 1-7). Urogenital trichomoniasis is usually transmitted during sexual contact between infected people or asymptomatic carriers of the disease. Non-sexual transmission can also occur. For example, mothers can infect their children during birth. It can also occur through the reuse of gloves during examinations. In addition, as the parasite can survive outside the body on infected items for a few hours, it can be transmitted through contact with infected diapers, bed-pans, toilet seats, and personal hygiene items (Isakov B. A., Zakharkiv Yu. F., Ermolenko D. K., et al. Diagnostics and treatment of urogenital trichomoniasis. Recommendations for physicians, St-Petersburg, Veliki Novgorod, 2006, p. 46).

A big significance in the epidemic process play people with weakly expressed symptoms and trichomonad carriers that facilitates the epidemiological spreading of the pathogen. Without treatment the protozoa survive in the body and cause numerous complications. Trichomoniasis has been diagnosed in 70 to 80-year old males who had their last sexual contacts 30 years ago.

Some medications, used for the treatment of trichomonas infection, lead to a relative reduction of symptoms. These drugs include acrichine, aminarson, dichloro-diphenyl-trichlorethane, and trichomycin. However, these substances are not very effective.

Women with urogenital diseases have been treated with phytotherapy that involved using extracts and tinctures obtained from onion, garlic, reddish, horseradish, pine and spruce needles, and jupiter.

Currently, metronidazole (synthesised in 1959) is widely used for the treatment of urogenital trichomoniasis. Widespread use was found for combination treatment methods, which included use of peroral and intravaginal drugs such as clion-D, gynalgin, tergynan, and metrogyl (Patent RU 2320319 "Vaginal suppositories", 2006.11.07). However, at present, there is no reliable method of trichomoniasis treatment.

Lately, treatment of trichomoniasis has become more difficult because of the appearance of new strains that are multiresistant to therapeutic substances. It has been established that chronic urogenital trichomoniasis taking place in a form of mixed invasion is a reliable indicator of occurrence of drugs resistant strains of *Trichomonas vaginalis*.

The existing treatment regimens often do not provide a significant effect as they do not take into account individual particularities of a patient. For example, the presence of concomitant diseases and changes in the immune system and the biological activity or resistance to therapeutic substances of the strain are not taken into consideration. Assessment of the sensitivity of *T. vaginalis* to antiprotozoal medications allows for a significant increase in the efficacy of treatment in patients with chronic urogenital trichomoniasis.

There are other pharmaceuticals such as mebendazole, butoconazole, and benzoisothiazolin (Vidal, Therapeutic substances in Russia, $6^{th}$ edition, 2000).

There is a need for development of new therapeutic substances for using shorter as well as more complex methods for treatment of urogenital trichomoniasis based on studies of pharmacokinetics and sensitivity of various strains of *T. vaginalis* to the same dose of used therapeutic substance (Narcisi E. M. In vitro effect of tinidazole and furazolidone on metronidazole-resistant *Trichomonas vaginalis*/E. M. Narcisi, W. E. Secor//Antimicrob. Agents Chemother.—1996.—Vol. 40. pp. 1121-1125; Zakharkiv Yu. F., Dependence of efficacy of etiotropic therapy of patients with trichomoniasis on sensitivity of strains of a pathogen to antiprotozoic drugs; Zakharkiv Yu. F., Poznyak A. L., Sidorchuk S. N., Gudkov P. B. Materials of the Russian Scientific Conference "Key issues in fighting infection", St-Petersburg, Military Medical Academy, 2004, pp. 192-193). Traditional anti-protozoan therapy leads to a significant improvement in the patient's condition and etiological recovery. However, clinical recovery does not occur in 64% of patients due to the development of post-trichomonal urethritis (PTU). In these cases, patients complain about unpleasant sensations during urination and periodic mucous-purulent discharge from the urethra (Vilkki M., Pukkala E., Nieminen P. et al. Gynecological infections as risk determinants of subsequent cervical neoplasia//Acta Oncol.—2000.—vol.—pp. 71-75). A thorough laboratory examination for the presence of trichomoniasis produces a negative result and additional anti-protozoan therapy is not successful. From clinical point of view, post-trichomonad urethritis has an undulating or monotonous character. Patients become irritable, have sleeping disorders, and can develop sexual dysfunction. The most frequent cause of PTU is the presence of other sexually transmitted pathogens. Urogenital trichomonas provides a depot for the survival of gonococci, fungi, chlamydiae, mycoplasma, and viruses (Thomason J. L. *Trichomonas vaginalis*/J. L. Thomason, S. M. Gelbert//Obstetrics and Gynaecology.—1989.—Vol. 74. pp. 536-541) since enzymes of protozoa cannot always destroy phagocytised by them microorganisms. Subsequently, these pathogens can support the inflammatory process for extended period of time. It has been established that trichomonas prevents the detection of chlamydia in cell culture. Clinically, inflammation due to mycoplasma and chlamydia occurs with relapses, often with damage to the accessory sexual glands. Development of PTU is facilitated not only by microflora that accompanies urogenital trichomoniasis, but also by the formation of L-form microorganisms and the reduction of immunobiological resistance in the host body. This also includes local immunity in the organs of the urinary system.

Recently, medical practitioners have found that treating urogenital trichomoniasis with metronidazole is ineffective. These failures can be related to low content of zinc in the blood (Debbia E. A. In vitro activity of metronidazole alone and in combination with clotrimazole against clinical isolates of *Trichomonas vaginalis*./E. A. Debbia, U. Campora, S. Massaro et al.//J. Chemother.—1996. Vol. 8, N2.—P. 96-101; Taru Meri I. T. Resistance of *Trichomonas vaginalis* to Metronidazole: Report of the First Three Cases from Finland and Optimization of In Vitro Susceptibility Testing under Various Oxygen Concentrations/I. T. Taru Meri, Sakari Jokiranta, I. Lauri Suhonen et al.//Journal of Clinical Microbiology.—2000.—Vol. 38.—No2. pp. 763-767), low absorption of the drug (Du Bouchet L. Multicenter comparison of clotrimazole vaginal tablets, oral metronidazole, and vaginal suppositories containing sulfanilamide, aminacrine hydrochloride, and allantoin in the treatment of symptomatic trichomoniasis/L. Du Bouchet, M. R. Spence, M. F. Rein et al.//Sex. Transm. Dis.—1997.—N3.—P. 156-60 Honigberg B. M. Structure of *Trichomonas vaginalis* Donne/B. M. Honigberg, V. M. King//J. Parasitol.—1964.—Vol. 50.—P. 345-364; Land K. M., Delggadillo-Corea M. G., Tachezy G. et al/. Targeted gene replacement of ferredoxin gene in *T. vaginalis* does resistance//Mol. Microbiol.—2004.—vol. 51.—P.115-120), and inefficient delivery of the drug to the vagina or inactivation of the drug by the vaginal flora (Borchardt K. A. A comparison of the sensitivity of the In Pouch TV, Diamond's and Trichosel media for detection of *Trichomonas vaginalis*./Borchardt K. A., Zhang M. Z., et al///J. Genitourin Med.—1997.—Vol. 4.—P. 297-298).

Other researchers suggest that the ineffectiveness of metronidazole could be due to previous multiple unsuccessful treatment attempts (Narcisi E.M. In vitro effect of tinidazole and furazolidone on metronidazole-resistant *Trichomonas vaginalis*/E. M. Narcisi, W. E. Secor//Antimicrob. Agents Chemother.—1996.—Vol. 40.—P. 1121-1125).

Resolving the issue of metronidazole-resistant organisms can be achieved by a number of ways. These include increasing the dose of metronidazole; use of a combination of various anti-trichomonas therapeutic substances, and using these substances in conjunction with nonspecific therapy (Narcisi E.M. In vitro effect of tinidazole and furazolidone on metronidazole-resistant *Trichomonas vaginalis*/E.M. Narcisi, W.E. Secor//Antimicrob. Agents Chemother.—1996.—Vol. 40.—P. 1121-1125).

Currently, urogenital trichomoniasis is treated with metronidazole and other nitroimidazoles, such as tinidazole, ornidazole, secnidazol, nimorazole, and carnidazole.

Metronidazole, which is included in individual and combined treatments of trichomoniasis, was selected as the comparator drug for the study described in this document.

SUMMARY OF INVENTION

The invention is a new therapeutic substance, of plant origin, that has minimal side effects when used as a treatment for various trichomonal infections.

The new therapeutic substance is an olive coloured paste. It is composed of a conifer green needle complex (CGNC) and has a coniferous smell and antiprotozoal activity against *T. vaginalis* (when tested in an in vitro model). CGNC also contains 35-40% water.

CGNC is an active ingredient in the therapeutic substance, Bioeffective A that is produced in an encapsulated form. It contains chlorophyll derivatives, carotenoids, vitamins A, E, and K, phytosterins, polyprenols, squalene, fatty and acid resin salts, natural antibiotics (phytoncides), essential oils, and other terpenoids (labdanic alcohols, aldehydes, and acids).

A range of concentrations (100, 200, 300, and 500 mg/ml) of CGNC was used to study the effect on *T. vaginalis* patient isolates. At a concentration of 100 mg/ml, CGNC exhibited trichomonadocitic and trichomonadostatic properties, and at 300 mg/ml suppressed the growth of *T. vaginalis*.

The authors studied the antiprotozoal activity of CGNC against such protozoan as *T. vaginalis* in a modelled system in vitro.

The results were compared with metronidazole, the medication traditionally used in the treatment of *T. vaginalis*. The parasitic protozoa, *T. vaginalis* was isolated from patients and cultured in vitro in nutrient media.

Nutrient medium (4.5 ml) was poured into sterile test tubes and covered with a 5 mm layer of Vaseline to create anaerobic conditions for the growth of trichomonas. Inoculation was carried out using a sterile Pasteur pipette. An aliquot (0.5-1.0 ml) of the test substance was dispensed in the bottom of the test tubes. The samples were incubated at 37° C. Examination of the test tubes to determine the presence of growth was carried out at 48 and 96 hours after inoculation. A dense, whitish deposit at the bottom of the test tube signified a positive result for trichomonas growth. This was sampled using a Pasteur pipette and prepared for microscopic analysis. The test sample was mixed with a drop of warm isotonic sodium chloride solution or Ringer-Locke solution and placed on a slide. The suspension was covered with a cover glass and observed under the microscopy (×600). The microscope used for this analysis was a MICMED-5 (LOMO, St-Petersburg). The number of protozoan cells in 1 ml of suspension was determined using a Goryaev chamber (as per the guidelines for the chamber).

In this study, a total of 150 people (80 male and 70 female) with inflammatory diseases of the urogenital tract were examined. The patient ages ranged from 17 to 45 years. Thirty isolates of *T vaginalis* were collected from this group. The clinical characteristics and demographics of this group of patients are presented in Table 1.

TABLE 1

Clinical characteristics and demographics of patients examined for the presence of *T. vaginalis*

| Clinical characteristics | Number of patients (% of total) | Age (years) |
| --- | --- | --- |
| Acute diseases of the urogenital tract (female) | 9 (6) | 19-23 |
| Acute diseases of the urogenital tract (male) | 10 (6.7) | 17-26 |
| Chronic diseases of the urogenital tract (female) | 32 (21) | 20-35 |
| Chronic diseases of the urogenital tract (male) | 37 (24.7) | 20-45 |
| Sterility (female) | 29 (19.3) | 28-35 |
| Sterility (male) | 33 (22.0) | 26-42 |
| Total | 150 (100) | 17-45 |

The study required isolation and selection of *T. vaginalis* isolates that were to be used in the in vitro model. Isolates were examined for various characteristics. These included the size and shape of the trichomonas, the pattern of their movement, and their intercellular content. Typically, the trichomonas were motile, pear, and occasionally oval shaped. Their sizes ranged from 13 to 17 μm, and they exhibited an impulse motion. In some cases, movement of the flagella was noticeable under the microscope. The nuclei of the trichomonas were not easily detected in unstained samples. The cytoplasm of trichomonas was generally grainy and vacuolated.

Then, the sensitivity of T. vaginalis to metronidazole was examined in vitro, using as an indicator the immobilisation of the trichomonad by the test-substance. For the sensitivity test, 90% or more of the protozoa were required to be motile. The sensitivity of T. vaginalis isolates to metronidazole was determined using serials dilution and the minimum inhibitory concentration (MIC) method. 4.0 ml of the medium was placed in test tubes and mixed with 0.5 ml of solution various concentrations of metronidazole—from 0.25 to 1000 μg/ml, or 1 mg/ml).

Then, 0.5 ml of pathogenic culture containing a known concentration of T. vaginalis (cells/ml) was added to the test tubes. Media without the test substance was used as a control. Vaseline was added to the surface (0.5 mm layer) of the tubes to create anaerobic conditions necessary for the growth of T.vaginalis. The test tubes were then placed in a thermostat at 37° C. Results were recorded 48 and 96 hours after inoculation.

The sensitivity of trichomonad to metronidazole was determined based on the minimum inhibitory concentration (MIC), which causes immobilisation of all cells of T.vaginalis. The strains were considered as resistant to metronidazole, when immobilisation occurred at concentration of metronidazole exceeding 15 μg/ml.

The MIC method cannot be used when atypical, amastigote (lacking flagella) T. vaginalis are present. Instead, a common in vitro lysis method for determining the sensitivity to antiprotozoal medications was used. Lysis of all trichomonas is an indicator of the efficacy of the test substance. Nutrient media containing trichomonas without metronidazole was used as a control. Metronidazole, at concentrations of 10, 15, 25, and 50 μg/ml was used in this experiment. Strains that lysed at a concentration of 25 μg/ml were considered resistant to metronidazole.

To determine sensitivity of clinical strains of Trichomonas vaginalis to CGNC, a method of cultivation on the medium for inoculation of trichomonas (MIT) was used. CGNC was added to the medium in a form of water solution with the final concentrations of 100, 200, 300, and 500 mg/ml. The control sample contained only suspension of trichomonad culture in nutritive medium.

The frequency of trichomonad detected in patients is shown in Table 2.

TABLE 2

Frequency of detection of Trichomonas vaginalis in various diseases of the reproductive system

| Nosological form | Total examined | Number of strains detected | Frequency of detection (%) |
|---|---|---|---|
| Acute diseases of urogenital tract (female) | 9 | 2 | 22.2 |
| Acute diseases of urogenital tract (male) | 10 | 2 | 20 |
| Chronic diseases of urogenital tract (female) | 32 | 5 | 15.6 |
| Chronic diseases of urogenital tract (male) | 37 | 9 | 24.3 |
| Sterility (female) | 29 | 4 | 13.7 |
| Sterility (male) | 33 | 8 | 24.2 |
| Total | 150 | 30 | 20 |

Of the 30 isolates of Trichomonas vaginalis, 3 actively motile and 7 amastigote were selected for further investigation.

Trichomonas, at a concentration of ≥$10^4$ cells/ml were added to nutrient media. The ability of the protozoa to replicate in artificial nutrient media was used as a selection criterion.

Characteristics of the trichomonas isolates and a description of clinical and anamnestic data of the patients are presented in Table 3.

TABLE 3

Demographic and clinical data on patients and characteristics of T. vaginalis strains included in study of anti-trichomonad activity of CGNC in vitro

| No. of strain | Sex | Age | Diagnosis | Data of anamnesis | Characteristics of strain |
|---|---|---|---|---|---|
| 1 | F | 19 | Acute vulvovaginitis | Patien B., first visit to doctor, first instance of disease, never had treatment | Actively mobile 5 × $10^4$ cells/ml |
| 2 | F | 20 | Acute colpitis | Patien K. first visit to doctor, first instance of disease, never had treatment | Actively mobile 3 × $10^4$ cells/ml |
| 3 | M | 17 | Acute urethritis | Patient P., first instance of disease, never had treatment | Actively mobile $10^4$ cells/ml |
| 4 | F | 24 | Chronic colpitis | Patient S., multiple visits to doctor. Has disease for 2 years, T. vaginalis detected for the first time. Metronidazole preventive treatment was used after the first visit to doctor; after that, symptoms of acute inflammation were removed. Reoccurrence after 5 months. Anamnesis contains 4 courses of antibiotic treatment without positive changes. | amastigote $10^4$ cells/ml |
| 5 | F | 41 | Chronic colpitis, chronic adnexitis | Patient K., multiple visits to doctor. Acute trichomoniasis 7 years ago. Had treatment with various medications, including metronidazole. | amastigote $10^4$ cells/ml |
| 6 | F | 28 | Chronic colpitis, secondary sterility | Patient E., first visit to doctor (doesn't consider herself as a patient). Was examined in relation to sterility and being in contact with other patients. T .vaginalis was detected for the first time. Her sexual partner has chronic trichomoniasis diagnosed 2.5 years ago. Had a course of preventive treatment with metronidazole. | amastigote 3 × $10^4$ cells/ml |

TABLE 3-continued

Demographic and clinical data on patients and characteristics of *T. vaginalis* strains included in study of anti-trichomonad activity of CGNC in vitro

| No. of strain | Sex | Age | Diagnosis | Data of anamnesis | Characteristics of strain |
|---|---|---|---|---|---|
| 7 | M | 22 | Chronic prostatitis | Patient M., first examination. After a casual sexual contact had characteristic discharges, did not go to doctor. Self-treated with metronidazole (as per instruction for use), that led to disappearance of acute symptoms. But, 2 months later, had periodic low abdominal pains. Considers himself to be sick for 8 months. | amastigote $10^4$ cells/ml |
| 8 | M | 38 | Chronic prostatitis | Patient P, multiple visits to doctor. Was diagnosed with acute trichomoniasis 14 years ago. Had a treatment in dermo-venereal clinic. First reoccurrence 8 months after the treatment. Had another course of anti-protozoal therapy (doesn't remember the name of medications) After the second course he had no subjective improvements that forced him to do self-treatment with analgesics during deterioration periods. Permanent stretching pains for the last 6 months pushed him to visit an urologist. | amastigote $5 \times 10^4$ cells/ml |
| 9 | M | 31 | Chronic prostatitis, sterility, expressed oligospermia, astenospermia | Patient I., first examination, pathogen is detected for the first time. Diagnosed with prostatitis 5 years ago. Twice had treatment against Chlamydia and ureaplasmic infections, which reoccurred 8-10 months after antibiotic therapy. Metronidazole was included in treatment of clamidiosis. | amastigote $10^4$ cells/ml |
| 10 | M | 30 | Chronic prostatitis, sterility, moderate astenospermia | Patient P., multiple visits to doctor. Acute trichomoniasis 12 years ago. Has no recollections about underwent treatments. Generally he feels good, but periodically has quickly passing stretching pains in small pelvis area related to consumption of alcohol, stress, fatigue and colds Examined in relation to infertility. | amastigote $10^4$ cells/ml |

Analysis of the sensitivity of various isolated strains of *T. vaginalis* to CGNC and metronidazole was conducted. The data from this experiment is shown in Table 4. Ten isolated strains of trichomonas were selected based on the selection criteria such as sufficient amount ($\geq 10^4$ cells/ml) and ability to multiply on the MIT were placed in test tubes with known amount of metronidazole or CGNC as per the method described in the section "Novelty of invention". Each test was repeated 3 times. Each isolate had a control such as medium for inoculation of trichomonas only—without any test-substance.

Table 4 shows that all actively mobile strains were detected in case of primary infection. Patients with the amastigote form of *T. vaginalis* had a history of infection and were treated with antiprotozoal medication.

TABLE 4

Effect of CGNC on clinical strains of *Trichomonas vaginalis*

| Isolate number | Control (number of trichomonads, cells/ml) | CGNC (number of trichomonas, cells/ml) | | | | Metronidazole, (MIC, µg/ml) |
|---|---|---|---|---|---|---|
| | | 100 mg/ml | 200 mg/ml | 300 mg/ml | 500 mg/ml | |
| 1 | actively mobile $5 \times 10^4$ cells/ml | weakly mobile $10^2$ | 0 | 0 | 0 | 15 |
| 2 | actively mobile $3 \times 10^4$ cells/ml | 0 | 0 | 0 | 0 | 15 |
| 3 | actively mobile $10^4$ cells/ml | weakly mobile $<10^2$ | 0 | 0 | 0 | 25 |
| 4 | amastigote $10^4$ cells/ml | amastigote $10^2$ | amastigote $<10^2$ | 0 | 0 | 50 |
| 5 | amastigote $10^4$ cells/ml | amastigote $<10^2$ | 0 | 0 | 0 | 25 |
| 6 | amastigote $3 \times 10^4$ cells/ml | 0 | 0 | 0 | 0 | 50 |
| 7 | amastigote $10^4$ cells/ml | amastigote $<10^2$ | amastigote $<10^2$ | 0 | 0 | 25 |
| 8 | amastigote $5 \times 10^4$ cells/ml | 0 | 0 | 0 | 0 | 25 |

TABLE 4-continued

Effect of CGNC on clinical strains of *Trichomonas vaginalis*

| Isolate number | Control (number of trichomonads, cells/ml) | CGNC (number of trichomonas, cells/ml) | | | | Metronidazole, (MIC, µg/ml) |
|---|---|---|---|---|---|---|
| | | 100 mg/ml | 200 mg/ml | 300 mg/ml | 500 mg/ml | |
| 9 | amastigote $10^4$ cells/ml | amastigote $10^3$ | amastigote $<10^2$ | 0 | 0 | >50 |
| 10 | amastigote $10^4$ cells/ml | amastigote $5 \cdot 10^2$ | amastigote $<10^2$ | <10 | 0 | 50 |

Legend
0-no *trichomonas* present
Data in Table 4 show that strains 4, 6, 9, and 10 were resistant to metronidazole (MIC was greater than 25 µg/ml).
Isolated strains 2, 6 and 8 were lysed at a CGNC concentration of 100 mg/ml (Table 4). It has also significantly reduced the number of protozoa in the rest of the samples in comparison to the control.
A CGNC concentration of 200 mg/ml inhibited all growth of isolates 1-6 and 8. The number of *trichomonas* isolates 7, 9 and 10 were significantly less than in the control sample (Table 4).
A concentration of 300 mg/ml CGNC inhibited all growth of isolates 1-9 (Table 4). Isolate no.10 contained only <10 cells/ml of *T. vaginalis*.
Addition of 500 mg/ml CGNC to nutrient media led to the death of protozoa in all 10 samples (Table 4).

Results from the study revealed that CGNC has antiprotozoal activity against *T. vaginalis* isolates obtained from the patient group (Table 4). A concentration of 100 mg/ml CGNC killed all trichomonas in 30% of cases and this concentration inhibited the growth of the organism in 70% of cases. At a concentration of 200 mg/ml, the test substance destroyed the pathogen in 7 samples (70%) and lowered the number of organisms in 3 cases (30%). CGNC at a concentration of 300 mg/ml killed 9 isolates (90%). CGNC killed both actively motile and amastigote trichomonas in all tested cases at this concentration. The correlation between the sensitivity of trichomonas to metronidazole and to CGNC was not established. Metronidazole, at 15 µg/ml had an effect on only 2 out of 10 isolates of actively motile trichomonas. The rest of the isolates were resistant to this antibiotic (Table 4).

An increase in the concentration of CGNC in the growth medium correspondingly reduced the amount of nutritive substances necessary for trichomonads. In the control samples of isolates 4, 5, 8 and 9 there was abundant growth of associated bacterial flora. There was no growth of microbial flora in samples of the same isolates containing CGNC at ≥300 mg/ml. The results obtained revealed anti-trichomonad activity of CGNC at concentration of 200 mg/ml. A correlation among the type of *T.vaginalis*, previous courses of treatment, or the effect of metronidazole was not found. The antibacterial effect of CGNC on the accompanying flora was noted in patients with urogenital tract dysbacteriosis that had developed after previous use of antibiotic therapy. The effective MIC for 4 test samples was ≥300 mg/ml. Clinical and literature data show that diseases caused by *T. vaginalis* are chronic, are poorly treated with currently available therapeutic substances (metronidazole and derivatives of 5-nitraimidazole, tinidazole, nimorazole, ornidazole, secnidazol, and derivatives of 4-aminoquinoline such as chloroquine and nitrofuran). The use of antibiotics with a wide spectrum of activity in diseases of the urogenital tract can lead to microbiocenosis of the urogenital tract. This condition reduces the effectiveness of local non-specific immunity and is the main reason for complaints on itchiness, burning, irritation and discharges with an unpleasant odour. It has been established that these conditions cannot be easily treated. The bactericidal effect of the test substance, CGNC, can prevent dysbacteriosis.

The study demonstrated the potential use of CGNC as a treatment for various trichomonas infections.

1. CGNC has antiprotozoal activity against ten *T. vaginalis* isolates obtained from patients with acute and chronic diseases of the urogenital tract.
2. The test substance demonstrated a trichomonacidal and trichomonastatic effect. The organism was killed in 30% of cases at a concentration of 100 mg/ml CGNC. There was an inhibitory effect on growth at this concentration in 70% of cases. The growth of *T. vaginalis* was inhibited in 90% of cases at a concentration of 300 mg/ml. 3. CGNC killed actively motile trichomonas and trichomonas without flagella.
4. A CGNC-related antibacterial effect on the associated flora was noted in patients with dysbacteriosis that had developed after the use of antibiotic therapy. Therefore, CGNC is effective as a therapeutic substance for the treatment of diseases associated with trichomoniasis.

EXAMPLES OF THE PREFERRED EXECUTION OF INVENTION

Below are Examples of Emulsion Based on the Therapeutic Substance

Example 1

CGNC—10.0 g
Double distilled water—made up to 100 g.

Example 2

CGNC—30.0 g
Double distilled water—made up to 100 g.

Example 3

CGNC—50.0 g
Double distilled water—made up to 100 g.

To prepare an emulsion (Examples 1-3), a mixing apparatus is loaded with calculated amount of CGNC, the paste is heated to 50° C., and calculated amount of double distilled water is added. Heating is stopped when the emulsion becomes homogeneous and the mixture is packed in glass bottles.

INDUSTRIAL APPLICATIONS

The results obtained from the study showed the potential use of CGNC as treatment for acute, chronic and asymptomatic trichomonas infections. The use of CGNC as antiprotozoal therapy allows for the acceleration of the treatment process, inhibition of *T. vaginalis* and associated pathogenic microflora in urogenital tract infections such as those found in dysbacteriosis.

The invention claimed is:

1. A method of suppressing the growth of *Trichomonas vaginalis* in a patient infected therewith, comprising administering to the patient an effective amount of a composition comprising conifer green needle complex (CGNC).

2. The method according to claim 1, wherein the concentration of CGNC in said composition is at least 100 mg/ml.

3. The method according to claim 2 wherein said composition has trichomonadocitic or trichomonadostatic effects.

4. The method according to claim 1 wherein the concentration of CGNC in said composition is at least 300 mg/ml.

5. The method according to claim 1 wherein the concentration of CGNC in said composition is at least 500 mg/ml.

6. The method according to claim 1, wherein the patient is suffering from acute or chronic *Trichomonas* infection.

7. The method according to claim 6 wherein said infection is an infection of the urogenital tract.

8. The method according to claim 1, wherein the patient is suffering from asymptomatic *Trichomonas* infection.

* * * * *